United States Patent [19]

Datta et al.

[11] Patent Number: 5,723,639
[45] Date of Patent: Mar. 3, 1998

[54] ESTERIFICATION OF FERMENTATION-DERIVED ACIDS VIA PERVAPORATION

[75] Inventors: Rathin Datta, Chicago; Shih-Perng Tsai, Naperville, both of Ill.

[73] Assignee: University of Chicago, Chicago, Ill.

[21] Appl. No.: 543,522

[22] Filed: Oct. 16, 1995

[51] Int. Cl.⁶ .................................................. C07C 51/00
[52] U.S. Cl. ........................ 554/154; 354/167; 354/170; 560/231; 560/234; 210/638; 210/640; 210/649; 210/650; 210/651
[58] Field of Search ..................... 554/167, 154, 554/170; 560/231, 234; 210/638, 640, 649, 650, 651

[56] References Cited

U.S. PATENT DOCUMENTS 2,956,070 10/1960 Jennings et al.

OTHER PUBLICATIONS

E.M. Filachione et al., Lactic Esters by Reaction of Ammonium Lactate with Alcohols, Sep. 1952, pp. 2189–2191, Industrial and Engineering Chemistry, vol. 44.

*Primary Examiner*—José G. Dees
*Assistant Examiner*—Deborah D. Carr
*Attorney, Agent, or Firm*—Cherskov & Flaynik

[57] ABSTRACT

A low temperature method for esterifying ammonium- and amine-containing salts is provided whereby the salt is reacted with an alcohol in the presence of heat and a catalyst and then subjected to a dehydration and deamination process using pervaporation.

The invention also provides for a method for producing esters of fermentation derived, organic acid salt comprising first cleaving the salt into its cationic part and anionic part, mixing the anionic part with an alcohol to create a mixture; heating the mixture in the presence of a catalyst to create an ester; dehydrating the now heated mixture; and separating the ester from the now-dehydrated mixture.

24 Claims, 1 Drawing Sheet

ESTERIFICATION OF FERMENTATION-DERIVED ACIDS VIA PERVAPORATION

CONTRACTUAL ORIGIN OF INVENTION

The U.S. Government has rights in this invention pursuant to Contract No. W-31-109-ENG-38 between the U.S. Department of Energy and the University of Chicago representing Argonne National Laboratory.

BACKGROUND OF THE INVENTION

1. Field of the Invention

This invention relates to a process for the esterification of organic acids, and more particularly, this invention relates to a method for a process for making high purity esters from fermentation derived organic acids using pervaporation processes.

2. Background of the Invention

Organic acids and esters of organic acids offer great feedstock potential for polymer and specialty product manufacture. Esters of organic acids are, by themselves, very valuable products, particularly as environmentally benign, non-toxic, non-halogenated solvents.

Demand for such "green" solvents continues to increase. For example, lactate esters such as ethyl lactate and butyl lactate have solvating properties similar to the more toxic ethylene glycol ethers. Lactate esters also can replace halogenated solvents, serve as intermediates for polymer production, and be converted to polymers by condensation. In as much as these acids and their corresponding esters are used as solvents, chemical or polymer feedstocks, and flavor and fragrance ingredients, they must be highly pure.

Fermentation-derived acids are always accompanied by some residual impurities such as simple sugars, carbohydrates, proteins, amino acids, and other organic and inorganic compounds. For example, a high-yield, crude fermentation broth engineered to produce lactic acid contains not only 80–90 grams per liter (g/l) lactate but also 10–20 g/l of contaminating (unfermented) carbohydrates, proteins, cell parts and other organics. These residual impurities usually have to be removed to attain the highly-pure products, as discussed supra, before their use as specialty chemicals.

Organic acids such as lactic, butyric, succinic, acetic and propionic acids are produced by fermentation of carbohydrates with anaerobic bacteria. Generally, the acids appear as ammonium-, sodium-, calcium-, and potassium-salts, with the cations initially introduced into the fermentation liquor as hydroxides or carbonates to maintain an optimal, near neutral pH for the bacteria. The salts are then converted to their respective acids by acidification with mineral acids, such as sulfuric, with production of the byproduct salt such as sodium, calcium or ammonium sulfate. However, the organic acids produced by this process are not suitable for certain polymerization processes or as chemical feedstocks.

Employing recently developed water-splitting electrodialysis procedures can eliminate the by-product salt and the corresponding alkali can be recycled to fermentation. However, the use of water-splitting processes requires an additional step.

A method to further purify the organic acids is through esterification whereby volatile alcohols such as methanol, ethanol or butanol are used to convert the desired organic acid to its ester, with the ester subsequently separated from the reaction liquor via distillation.

Drawbacks to using volatile alcohols in typical high temperature esterification processes are numerous. First, alcohols, with their lower boiling points compared to esters, vaporize without reacting efficiently with the acid. Large molar excesses of alcohol therefore have to be used, vaporized, and re-condensed, all of which leads to increased costs and energy use.

The use of volatile alcohols also leads to the formation of azeotropes, some of which are low boiling. These compounds have to be broken down by further solvent-distillation to remove the water and make the ester.

Also inherent with high temperature esterification procedures is the formation of undesirable products. For example, in the presence of the esterification catalyst (typically acidic), the impurities in the crude acid form large amounts of thermal- and acid-catalyzed breakdown contaminants. Some of the impurities are derived from the residual carbohydrates which under acid catalyzed conditions produce aldehydes. These aldehydes interfere with subsequent chemical conversion or polymerization reactions, and many have undesirable odor. Other impurities are derived from the residual carbohydrates and proteins which can react to make colored residues or tars or Malllard reaction byproducts.

As a result of the above-identified problems associated with volatile alcohol use in esterification processes, the costs of final product are large. For example, the step of making methyl lactate from lactic acid increases costs by $0.10 per pound, and requires 5–6 pounds of steam. Therefore, traditional esterification processes currently are not economically viable if fermentation-derived organic acids are used as polymer or chemical feedstocks, compared to petrochemical feedstock sources.

One of the main technical problems of making an ester is the removal of water from the reaction mixture without removing the alcohol, and thus driving the reaction, depicted in Equation 1, below, to the right where R—COOH is the carboxylic acid, R'—OH is the alcohol, and $RCO_2R'$ is the ester.

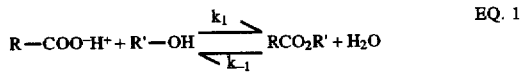

$$R-COO^-H^+ + R'-OH \underset{k_{-1}}{\overset{k_1}{\rightleftharpoons}} RCO_2R' + H_2O \qquad \text{EQ. 1}$$

The challenge for esterification of ammonium and amine-based salts, such as ammonium carboxylate is the removal of ammonia and water, as they are formed, but without removing the alcohol, thus driving the reaction, depicted as Equation 2, to the right.

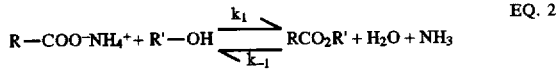

$$R-COO^-NH_4^+ + R'-OH \underset{k_{-1}}{\overset{k_1}{\rightleftharpoons}} RCO_2R' + H_2O + NH_3 \qquad \text{EQ. 2}$$

As first disclosed in E. M. Filachione, et al. *Industrial and Engineering Chemistry*, 44, 2189–2190, typical processes for producing esters from ammonium carboxylates require high temperatures, up to 200° C. In these high temperature processes, only higher boiling alcohols such as butanol or longer chain alcohols are usable so as to minimize alcohol volatilization. Also, large excesses of the alcohol are necessary. Furthermore, the process produces reaction by-products that are not esters. As such, typical esterification procedures of ammonium carboxylates also can prove costly, and still do not provide highly pure esters.

A need exists in the art to provide a more efficient method of esterification of fermentation-derived organic acids. The method should employ fewer production steps, use less energy, use lower boiling alcohols, and provide purer yields of esters. The esters subsequently can be used as solvents or for chemical and polymer feedstocks.

SUMMARY OF THE INVENTION

An object of the present invention is to provide a method for esterification of organic acids that overcomes many of the disadvantages of the prior art.

Another object of the present invention is to provide a method for production of organic acids which will yield high grade product for use as chemicals or feedstocks. A feature of the invention is the incorporation of pervaporation in the esterification process of the organic acid purification procedure and a lowering of reaction temperatures. An advantage of the invention is the elimination of the need for large amounts of volatile alcohols and therefore a lowering of costs associated with esterification procedures.

Yet another object of the present invention is to provide an improved method for production of high grade esters from fermentation-derived ammonium carboxylates. A feature of the method is the direct conversion of the ammonium carboxylates to the ester, without first converting to its respective acid. An advantage of the method is the elimination of the use of a salt-cleaving step, such as the addition of mineral acid, thereby conferring cost savings and eliminating waste salt byproduct.

Briefly, the above objects and advantages of the present invention are achieved by a method for esterifying an ammonium salt comprising obtaining the ammonium salt from a fermentation reaction; mixing the ammonium salt with an alcohol to create a mixture; heating the mixture in the presence of a catalyst; and subjecting the mixture to a pervaporation process The invention also provides for a method for purifying esters of organic acids comprising splitting or converting the salt into its cationic and anionic part (i.e. acid and base, respectively); mixing the anionic part (acid) with an alcohol to create a mixture; heating the mixture in the presence of a catalyst to create an ester; dehydrating the now heated mixture; and separating the ester from the now-dehydrated mixture.

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

Figure 1:
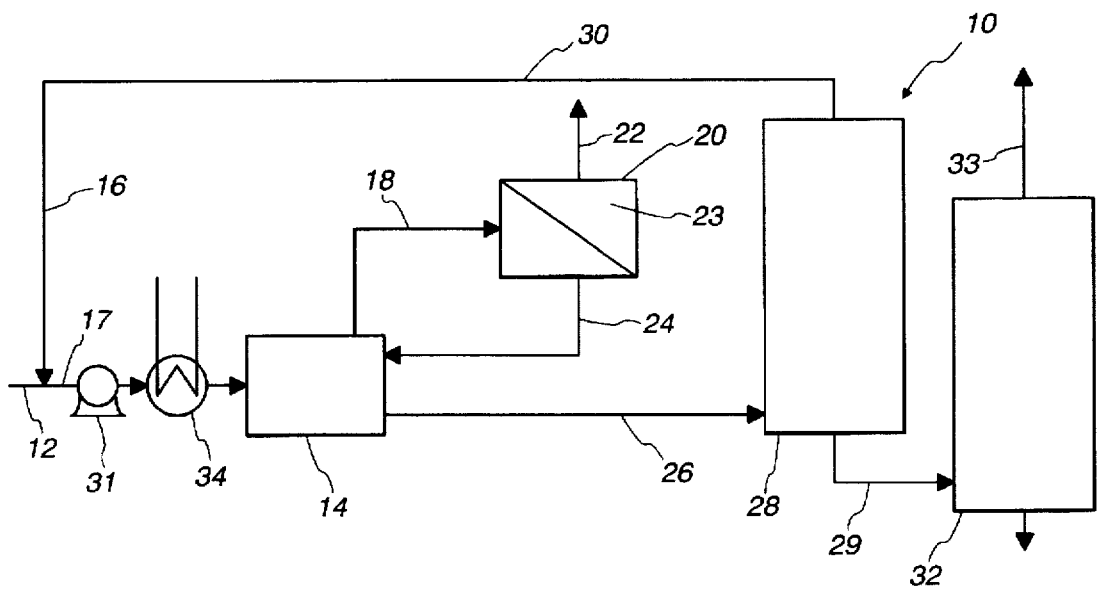
FIG. 1 is a schematic diagram of an exemplary ester production and purification process in accordance with the present invention.

A very facile, and low-energy-requiring process to make volatile alcohol esters from fermentation-derived ammonium carboxylates and other organic acids has been developed. The process employs certain hydrophilic pervaporation membranes that pass ammonia and water vapor without passing any volatile alcohol, and at relatively low temperatures of less than 100° C. This process removes ammonia from any of the thermally cracked ammonium salts while minimizing any loss of volatile alcohol from the reaction mixture to assure high yields and conversions. Aside from ammonium-based carboxylates, the process generally is applicable for the conversion of weak, volatile bases which have boiling points at or below 120° C. Such material in this category include the ammonium and amine salts and also the amides, such as the pyridines The invented process eliminates the need for high heat applications in the refining process of fermentation-derived organic acids, thereby minimizing the occurrence of side reactions between fermentation liquor impurities which would otherwise lead to unwanted by-products.

This pervap-assisted esterification process can be used for a wide range of fermentation-derived carboxylates. The following examples disclosed infra for ethyl esterification of lactic acid, ammonium lactate, ammonium propionate and butyl esterification of butyric acid are meant to be illustrative of the wide ranging utility of the invention, and are not to be construed as limitations to the invented process.

A laboratory scale pervap/esterification system manufactured by Zenon (Burlington, Ontario) and modified by the inventors was utilized. A simplified schematic diagram of the system is designated as numeral 10 in FIG. 1.

The invented process 10 consists generally of a liquid recirculation loop, a flat-cell pervaporation purifier and a permeate collection point. At the beginning of the process, a feed solution, 12, consisting of an aqueous solution of an organic acid, such as ammonium lactate, is supplied from a fermentation process stream. Typically, this stream is obtained by concentration and partial purification of the lactate in the fermentation broth by a separation process such as desalting electrodialysis or other means, followed by further concentration by evaporation. In instances where an organic acid is not supplied as an ammonium salt, the salt is first converted to the acid prior its mixture with other reactants in this process.

The feed solution 12 is combined with an alcohol feed stream 16 to create a reactants mixture 17. A myriad of alcohols are applicable, including, but not limited to, methanol, ethanol, propanol, isopropanol and butanol. Generally, alcohols containing from one to four carbons are preferred. Mole ratios of the alcohol to the carboxyl group will vary but generally will range from approximately 1:1 to 6:1. The resulting mixture is then directed to an esterification reactor 14. Alternatively, the alcohol and the feed solution can be placed separately in the esterification reactor with mixture of these two reactants occurring inside the reactor.

The alcohol reacts with the lactate in the esterification reactor 14 in the presence of a homogeneous or heterogeneous catalyst. If a heterogeneous catalyst is used, the reactor 14 will include a containment device, such as a packed bed, for the catalyst. A first product stream of the esterification reaction is directed via a product transport means, such as a conduit 18, to a reaction product separator 20. If the product is a liquid, the reaction product separator 20 will be a pervaporation unit. If the product is a vapor, a vapor permeation unit will be used as the reaction product separator 20. Depending on the carboxylic salt esterified, a myriad of pervaporation membranes are applicable, as noted below. Generally, the membranes are designed to remove water from the reaction mixture so as to shift the reaction further to the right. In the case of ammonium salts, the membrane would also be ammonia (ammonium hydroxide) permeable so that both water and ammonia are selectively removed from the product mix of the esterification process.

A low pressure means 22 such as a vacuum or sweeping gas is applied to the permeate chamber 23 to facilitate removal of the permeating water and/or ammonia via vaporization or fluid collection. (One means for creating a vacuum is through the utilization of the pressure drop resulting from the condensation of the permeating vapors.) Generally, vacuum pressures of approximately 50 to 75 torr for industrial processes and 100 to 150 torr for laboratory-scaled conversions provide good results. Preferably, the reactor 14 is maintained as a closed system to avoid excessive vaporization of the alcohol in the reaction mixture. The pressure in reactor 14 is autogenous and is thus dependent on temperature and composition and is generally lower than 200 psig.

A means for returning the retentate 24, such as a conduit, is employed to return the retentate back to the esterification reactor 14 for additional conversion. This additional conversion is facilitated in as much as equilibrium constraints have been relieved by removing products of the reversible reaction.

A second product stream of the esterification reaction, containing ester, excessive alcohol and small amounts of water, impurities, and unconverted lactate such as ammonium lactate, is directed via a second product stream directing means 26 to a first distillation means 28, such as a thermal column. The distillation means 28 removes alcohol from the second product stream, with the alcohol redirected via a recirculation loop 30, aided by a recirculation pump 31, to combine with the alcohol feed stream 16. The higher fractions 29 resulting from this first distillation process, including impurities and the desired ester, are directed to a second distillation means 32 for further processing. Purified ester is obtained here as distillate 33. Bottom fraction of this second distillation process, consisting of unconverted lactate, impurities and by-products, can be used as fuel or recycled for lactate recovery.

Reaction temperatures in the esterification reactor can range from 50° C. to 200° C., more typically from between 80° C. and 150° C., and ideally from between approximately 75° C. and 120° C. Lower temperatures, relative to those employed in typical esterification procedures, are desired to avoid plasticization of pervaporation membranes. Such temperatures are regulated by a temperature regulating means 34, such as a thermostatically controlled heater, which can be located just upstream of the esterification reactor 14, as shown, or else integrally connected to the esterification reactor.

Figure 2:
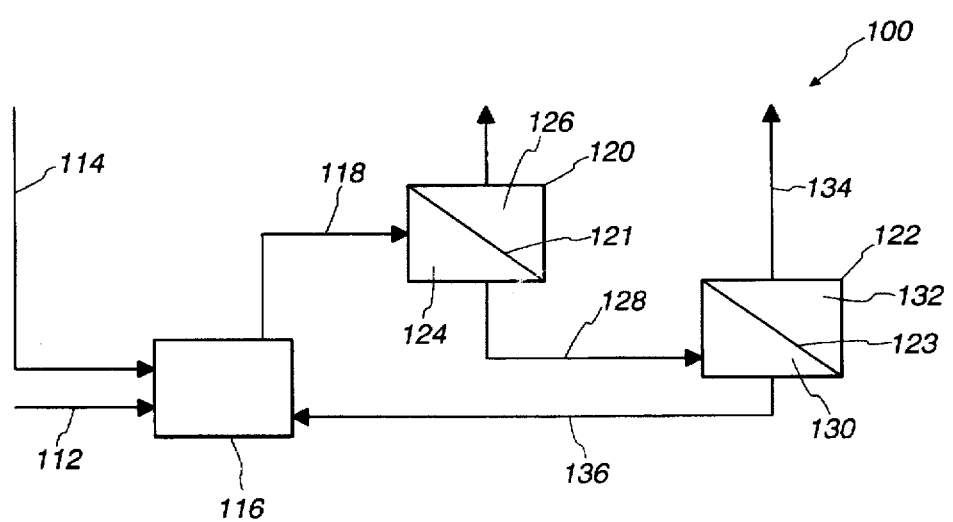
FIG. 2 is a schematic diagram of an exemplary ester purification process utilizing a plurality of pervaporation units, in accordance with the present invention.

Another exemplary embodiment of the invention is depicted in FIG. 2 as numeral 100 whereby a plurality of pervaporation membranes are utilized. A feed solution 112 as a fermentation-derived, aqueous solution containing the desired organic acid as a salt, such as ammonium lactate, is first concentrated and partially purified as in the first embodiment. These concentration and purification steps are not shown. In the case of ammonium lactate, the feed solution 112 contains 60 to 80 percent concentration of the lactate in water and small amounts of residual carbohydrates, proteins, amino acids, mineral salts, etc. The feed solution is initially placed into an esterification reactor 116.

An alcohol feed stream 114 is also fed into the esterification reactor 116. Alternatively, and as is shown in FIG. 1, the alcohol feed stream 114 is combined with the feed solution to create a mixture, which in turn is placed into the esterification reactor 116.

With all reactants present in the reactor 116, reaction occurs in the presence of a homogeneous or heterogenous catalyst. Catalyst types, reaction temperatures, and pressures are similar to those disclosed in the operation of the process 10 depicted in FIG. 1.

A first product stream 118, either of liquid- or vapor-phase, is directed from the esterification reactor 116 to a first membrane separation unit 120, and subsequently to a second membrane separation unit 122. If the first product stream 118 is a liquid, the membrane separation units 120, 122 are pervaporation units. If the first product stream 118 is a vapor, then the membrane separation units 120, 122 are vapor permeation units. The membrane separation units 120, 122 comprise two chambers separated by a first membrane 121 and a second membrane 123 respectively. A first upstream-side chamber 124, or feed/retentate chamber accommodates the incoming first product stream 118, while a first permeate chamber 126 is adapted to receive water, and in the case of ammonium carboxylate processing (or other amine-salt processing), ammonia, amine salts such as triethylammonium lactate, and volatile amines such as trimethylamine and triethylamine. As such, the first membrane 121 possesses such selectivity that it can effectively permeate water and ammonia and effectively retain alcohol and ester. As noted infra, several commercially available membranes, comprising a polyvinyl alcohol-based hydrophilic selective layer, have shown such separation selectivity. A vacuum which is generated either by condensation of the volatile permeate, or a sweeping gas (i.e., nitrogen, helium, argon, or any other inert gas) is applied to the permeate chamber to facilitate removal of the permeated water and nitrogen-containing permeates, with these permeates recycled for use in the fermentation process.

A first retentate feed stream 128 is then directed to a second feed/retentate chamber 130 in the second membrane separator 122 containing the second membrane 123. The second membrane 123 possesses such selectivity that results in the effective permeation of the product ester while retaining the alcohol, lactate and water.

A vacuum, created by condensation of the vapor, or sweeping gas is applied to the downstream side or second permeate chamber 132 to facilitate removal of the permeated ester which is considered a final product stream 134. The remaining second retentate stream 136 is then directed back to the esterification reactor 116 for further conversion, thereby further facilitating reaction equilibrium shift to the right.

Catalyst and Membrane Detail

Many esterification or transesterifcation catalysts can be utilized in the esterification units 14 and 116. These catalysts include sulfuric acid, p-toluene sulfonic acid (p-TSA), 4-dimethyl aminopyridine (DMAP), stannous octoate, lipases, esterases, the acidic resins such as those marketed under the Amberlyst trade name, and long chain non-volatile amines such as the $C_8$–$C_{10}$ straight-chain tertiary amine mixture marketed as Alamine 336 (Henkel Corp., Gulph Mills, Pa.). The DMAP and amine catalysts are particularly applicable in ammonium carboxylate conversion processes.

One type of resin, marketed as Amberlyst 15™ and Amberlyst XN 1010™ by Rohm and Haas Co., Philadelphia, Pa., consists of a bead form macroreticular, strongly acidic resin, having a polymeric matrix of sulfonated polystyrene that is cross-linked with divinylbenzene.

Water is selectively removed from the reaction mixture by its transport through the pervaporation membrane contained in the pervaporation purifier 20. While the effective area of the pervaporation membrane used for the following examples was from 62.5 to 182 square centimeters ($cm^2$), surface areas of the membrane can vary, depending on flow rates and viscousness of the fermentation liquor. Generally, flux rates, measured in kilograms per square meter per hour (kg/m²/hr) of from 0.08 to 3 are obtainable, with flux rates of 0.1 to 1 kg/m²/hr preferred.

Generally, the pervaporation membrane employed consists of a nonporous polyvinyl alcohol-active layer or a nonporous organophilic polydimethylsiloxane-active layer on a porous supporting layer and resistant to certain, desired products. Membranes with a polyvinyl alcohol-based hydrophilic selective layer effectively permeate water and ammonium while retaining alcohol and ester. For example, membranes manufactured by GFT in Neunkirchen-Heinitz, Germany, as the GFT PerVap 1001 or 1005 names consist of a membrane with a non-porous polyvinyl-alcohol active layer on a porous supporting layer made of polyester and polyacrylonitrile, to provide resistance to organic acids. An alkali-resistant membrane, marketed as GFT PerVap 2001 consists of a non-porous polyvinylalcohol active layer on a porous supporting layer made of polyacrylonitrile. Another applicable organic acid-resistant membrane is marketed as TexSep 1B, and consists of a membrane with a non-porous polyvinyl-alcohol (PVA) active layer on a porous supporting layer, resistant to organic acids.

Generally, hydrophobic compounds can be used as the active layer of organic permeable membranes. As such, membranes incorporating polydimethylsiloxane in their organic permeable active layer, such as GFT Per Vap 1170™ membrane from Neunkirchen-Heinitz, Germany, provide ester selectivity. Other examples of hydrophobic compounds used as constituents of the active layer include copolymers of styrene and styrene derivatives, polyether block amides, and polytrimethylsilylpropyne.

EXAMPLE 1

Ethyl esterification of lactic acid was carried out by reacting ethanol with lactic acid. The initial feed solution contained 55.4 weight percent ethanol, 37.5 weight percent lactic acid and 6.7 weight percent water. The molar ratio of ethanol to lactic acid was 2.8 in the feed. The lactic acid used was a commercial food grade fermentation-derived lactic acid. Corn steep liquor and maltose were added to the feed, each at 0.5 weight percent of lactic acid, to simulate the impurities that are typically present in the fermentation-derived lactic acid after primary purification. Identical feed solutions were placed into the pervap/esterification system and a simple flask reactor for parallel esterification experiments. In both systems, the catalyst was Amberlyst 15 at 3 weight percent of lactic acid.

In the pervaporation assisted esterification process, the pervaporation membrane was the GFT Pervap 1005. The membrane surface area was 62.5 cm². The temperature of the reaction mixture was maintained at 80° C., and the permeate side vacuum pressure was 4–25 millibar (mbar). The reaction temperature in the simple flask reactor was 86° C., which was the boiling temperature of the reaction mixture. After 166 hours, the reaction was terminated in both systems.

The conversion in the pervaporation assisted esterification was found to be 90 percent, compared with the 75 percent conversion for the simple flask esterification. The performance of the pervaporation separation was found to be satisfactory. The membrane selectivity for water over ethanol was 700 and the average water flux was 0.18 kg/m²/h, ranging from 0.49 kg/m²/h at 9 percent water to 0.1 kg/m²/h at 3.2 percent water.

EXAMPLE 2

Ethyl esterification of lactate (in ammonium lactate) was conducted by reacting ethanol with ammonium lactate. The initial reactant mixture 17 contained 36.6 weight percent ethanol, 42.5 weight percent ammonium lactate and 20.9 weight percent water. The molar ratio of ethanol to lactate in the feed was 2.0. The ammonium lactate solution was prepared from neutralization of a commercial 88 percent lactic acid solution with ammonium hydroxide.

Identical feed solutions were placed into the pervap/esterification system and the control process as outlined supra, which was a simple flask reactor. In both systems, the catalyst was 4-dimethylaminopyridine (DMAP) at 1.0 weight percent of ammonium lactate. In the pervap-assisted esterification, the pervaporation membrane was the GFT PerVap 2001. Temperature of the reaction mixture was maintained at 95° C. Permeate side vacuum pressure was between 37 and 100+torr. Permeate was collected by a combination of five cold traps and acid traps in series, arranged as follows: cold trap #1 (dry ice-acetone mixture), 3.0M sulfuric acid trap #1, 3.0M sulfuric acid trap #2, cold trap #2 (approximately −45° C.), and cold trap #3 (dry ice-acetone mixture). Acid traps were changed during the experiment. The water flux decreased from 0.50 kg/m²h to 0.12 kg/m²/h during the experiment (based on the mass of permeate collected by cold trap #1), indicating a decrease in water content of the reaction mixture. The reaction temperature in the simple flask reactor was 84° to 85° C., which was the boiling temperature of the reaction mixture. After 104 hours, the reaction was terminated in both systems. The membrane surface area was 182 cm².

Reaction mixture samples were taken during the experiment and analyzed; ethyl lactate and lactamide concentrations were measured by HPLC and ammonium lactate concentrations were measured by an ammonium electrode. The final concentrations in the reaction mixture from the pervap-assisted esterification were 4.3 weight percent ethyl lactate and 4.7 weight percent lactamide, compared to 2.4 weight percent and 1.5 weight percent respectively from the simple flask reaction. Lactate conversion was 12.1 percent from the pervap assisted esterification, compared with 7.6 percent from the simple flask reaction, showing an approximately 60 percent increase due to the invented process.

Ammonium concentrations in the two acid traps were measured by ammonium electrode and found to range from 884 ppm to 4,410 ppm. Cold trap #1 samples were analyzed by HPLC, and ethanol and ethyl lactate concentrations were found to be below the detection limit.

EXAMPLE 3

Ethyl esterification of ammonium lactate was repeated without the use of 4-dimethylaminopyridine. The reactant mixture contained 36.6 weight percent ethanol, 42.5 weight percent ammonium lactate and 20.9 weight percent water. The molar ratio of ethanol to lactate was 2.0. Identical reactant mixtures were placed into the pervap/esterification system and in the control flask reactor. No esterification catalyst was used for either system. In the pervap-assisted esterification, the pervaporation membrane was the GFT PerVap 2001. The temperature of the reaction mixture was maintained at 95° C., and permeate vacuum pressures ranged from between approximately 37 and 53 torr. The water flux was measured as 0.57 kg/m²/h between elapsed times of 18 and 21 hours flux (based on the mass of permeate collected by cold trap #1). The membrane surface area was 182 cm².

Permeate was collected by a combination of five cold traps and acid traps in the following series: cold trap #1 (dry ice-acetone mixture at −70 ° C. or 2° C.), acid trap #1 , acid trap #2, cold trap #2 (approximately −45° C.), and cold trap #3 (dry ice-acetone mixture). 1.5M sulfuric acid was used (instead of 3.0M) in the acid traps. Acid traps were changed during the experiment. The reaction temperature in the simple flask reactor was 84°–85° C., which was the boiling temperature of the reaction mixture. After 49 hours, the reaction was terminated in both systems.

Reaction mixture samples were taken during the experiment and analyzed; ethyl lactate and lactamide concentrations were measured by HPLC. Final concentrations in the reaction mixture from the pervap-assisted esterification were 5.5 weight percent ethyl lactate and 2.9 weight percent lactamide, versus 3.0 weight percent and 1.2 weight percent respectively for the control reactor. The estimated lactate conversion was 14.5 percent from the pervap assisted esterification, compared with 7.9 percent from the control reactor, showing an almost 84 percent increase due to the invented process.

Ammonium concentrations in the two acid traps, as measured by ammonium electrode, ranged from 436 ppm to 1,458 ppm.

EXAMPLE 4

Ethyl esterification of lactate (in ammonium lactate) was carried out by reacting ethanol with ammonium lactate. The initial feed solution contained 63.8 weight percent ethanol, 24.7 weight percent ammonium lactate, and 11.5 weight percent water. The molar ratio of ethanol to lactate in the feed was 6.1. The ammonium lactate solution was prepared from neutralization of a commercial 88 percent lactic acid solution with ammonium hydroxide solution.

Identical reactant mixtures were placed into the pervap/esterification system and the flask reactor control. In both systems the catalyst was 4-dimethylaminopyridine (DMAP) at 10 weight percent of ammonium lactate.

In the pervap-assisted esterification, the pervaporation membrane was the GFT PerVap 2001. Membrane surface area was 182 cm$^2$. Temperature of the reaction mixture was maintained at 95° C. Permeate-side vacuum pressure ranged from between approximately 53 and 73 torr. Permeate was collected by a combination of four cold traps and acid traps in series, arranged in the following order: cold trap #1 (dry ice-acetone mixture or 2° C.), 1.5M sulfuric acid trap #1, 1.5M sulfuric acid trap #2, and cold trap #2 (approximately −45° C.). Acid traps were changed during the experiment. The permeate flux (based on the mass of permeate collected by cold trap #1) was measured as 0.36 kg/m$^2$/h between elapsed times of 14 and 18 hours. The reaction temperature in the simple flask reactor control was 81° to 82° C., which was the boiling temperature of the reaction mixture. After 71 hours, the reaction was terminated in both system and the products were analyzed.

Concentrations of unreacted ammonium lactate, calculated by the ammonium concentrations measured by ammonium electrode were 18.9 weight percent in the pervap-assisted esterification process and 22.8 weight percent in the control process. Concentrations of ethyl lactate, as measured by HPLC, in the pervap-assisted process was 2.9 weight percent versus a 1.1 weight percent yield in the control flask. The estimated lactate conversion was 14.5 percent in the pervap-assisted esterification, compared to 7.2 percent in the control process, showing an approximately 100 percent increase attributable to the invented process.

EXAMPLE 5

Ethyl esterification of propionate (in ammonium propionate) was conducted by reacting ethanol with ammonium propionate. The reactant mixture contained 67.7 weight percent ethanol, 22.3 weight percent ammonium propionate and 9.9 weight percent water. The molar ratio of ethanol to propionate in the reactant mixture was 6.0. The ammonium propionate solution was prepared from neutralization of a commercial 100 percent propionic acid solution with ammonium hydroxide solution. Identical reactant mixtures were placed into the pervap/esterification system and the control flask configuration. Both systems utilized the esterification catalyst 4-dimethylaminopyridine (DMAP) at 5 weight percent of ammonium propionate. The pervaporation membrane used was the GFT PerVap 2001, and had a surface area of 182 cm$^2$. Temperature of the reaction mixture was maintained at 95° C., and permeate side vacuum pressure was between 48 and 70 torr. The permeate was collected by 5 cold traps and acid traps arranged in the following order: cold trap #1 (either dry ice-acetone mixture or 2° C.), 1.5M sulfuric acid trap #1, 1.5M sulfuric acid trap #2, cold trap #2 (approximately −45° C.), and cold trap #3 (dry ice-acetone mixture). Permeate flux was measured as 0.48 kg/m$^2$/h between elapsed times of 3 and 6 hours (based on the mass of permeate collected by cold trap #1). The reaction temperature in the simple flask reactor was 81° C., which was the boiling temperature of the reaction mixture. The reaction was terminated in both systems after 76 hours.

Analysis of the permeate revealed concentrations of 8.8 weight percent ethyl propionate, compared to 1.9 weight percent in the control process. Propionate conversion was estimated at 40.7 percent in the pervap-assisted esterification, compared to 4.7 weight percent in the control process, or an approximate 760 percent increase attributable to the invented process.

EXAMPLE 6

Ethyl esterification of lactic acid was carried out by reacting ethanol with lactic acid. The initial reactant mixture contained 41 weight percent ethanol, 32.1 weight percent lactic acid, and 26.9 weight percent water. The mole ratio of ethanol to lactate in the feed was 2.0.

The lactic acid used was a commercial lactic acid. Corn steep liquor and maltose were each added at 0.5 weight percent to simulate the impurities typically present in fermentation broth after primary purification. The esterification catalyst was para-toluene sulfonic acid (pTSA) added at 1 weight percent of lactic acid. The pervaporation membrane was GFT PerVap 1005, and had a surface area of 182 cm$^2$. Temperature of the reaction mixture was maintained at 80° C., and the permeate-side vacuum pressure was approximately 3 millibar. (1 millibar=0.75 torr). The reaction was terminated after 8 hours.

Final reaction product contained 20.5 weight percent ethyl lactate, 32.9 weight percent ethanol, 27.7 weight percent water and 18.9 weight percent lactic acid. The average water flux was 1.15 kg/m$^2$/h. The permeate contained greater than 98 weight percent water and less than 2 weight percent ethanol.

EXAMPLE 7

Ethyl esterification of lactic acid was carried out by reacting ethanol with lactic acid. The reaction system had a larger flat-cell pervaporation module (effective area of 182 cm$^2$) and the sizes of other components were upgraded. Initial feed solution contained 47.4 weight percent ethanol, 46.3 weight percent lactic acid and 6.3 weight percent of water. Molar ratio of ethanol to lactic acid was 2.0 in the feed. The lactic acid used was a commercial food grade fermentation-derived lactic acid. Corn steep liquor and maltose were added to the feed, each at 0.5 weight percent of lactic acid, to simulate the impurities that are typically present in the fermentation-derived lactic acid after primary purification. Amberlyst XN-1010 was used at the catalyst at 10 weight percent of lactic acid. The pervaporation membrane was the GFT PerVap 1005. Temperature of the reaction mixture was maintained at 95° C., and the permeate-side vacuum pressure was less than 0.5 mbar. After 81.7 hours, the reaction was stopped.

Final reaction product consisted of 76.3 weight percent ethyl lactate, 23.2 weight percent ethanol, and 0.5 weight percent lactic acid. Water concentration was below detection limits. Average water flux was 0.41 kg/m$^2$/hr, and ranging from 1–3 kg/m$^2$/hr at greater than 7 weight percent water to less than 0.1 kg/m$^2$/hr at low water concentrations (for example below 0.4 weight percent).

Conversion in this pervap-assisted esterification process was greater than 99 percent.

EXAMPLE 8

This example is based on the process depicted in FIG. 2 whereby organic compound-permeable pervaporation membranes are utilized, instead of distillation, to separate ester from final product liquors.

One thousand, five hundred (1,500) grams of a feed, simulating an esterification reaction mixture containing 21 weight percent lactic acid, 34.4 weight percent ethanol, 31 weight percent ethyl lactate, and 13.6 percent water, was fed to the pervap-assisted esterification system. The GFT Per-Vap 1170 was the pervaporation membrane used, with an effective area of 62.5 cm$^2$.

The mixture was subjected to pervaporation at 80° C. The permeate-side vacuum pressure was approximately 8 mbar. The permeate was condensed and collected in a cold trap. After 20.4 hours, separation of the ester by pervaporation was terminated with a final retentate composition of 22.6 weight percent lactic acid, 34.9 weight percent ethanol, 13.6 weight percent water and 29 weight percent ethyl lactate. The permeate samples were found to contain 91.3–91.9 weight percent ethyl lactate, 4.5 to 4.8 weight percent ethanol, 1.6–2.3 weight percent lactic acid and 1.6–1.8 weight percent water.

Ethyl lactate was selectively removed from the reaction mixture to the permeate by using pervaporation. The ethyl lactate flux was 0.08–0.09 kg/m$^2$/h.

EXAMPLE 9

Butyl esterification of butyric acid was carried out by reacting butanol with butyric acid. The initial feed solution contained 63.2 weight percent butanol, 30.3 weight percent butyric acid, and 6.2 weight percent water. The molar ratio of butanol to butyric acid in the feed was 2.5. The butyric acid used was a commercial reagent-grade butyric acid. Corn steep liquor and maltose were added to the feed, each at 0.5 weight percent of butyric acid, to simulate the impurities that are expected to be present in the fermentation-derived butyric acid after primary purification. The same feed solution was placed into the pervap/esterification system and the simple flask reactor for parallel esterification experiments. In both systems, the catalyst was Amberlyst 15 at 5 weight percent of butyric acid. In the pervap-assisted esterification, the pervaporation membrane was the TexSep 1B, with a surface area of 62.5 cm$^2$.

The temperature of the reaction mixture was maintained at 80° C., and the permeate side vacuum pressure was 3–17 mbar. The reaction temperature in the simple flask reactor was 93° C., which was the boiling temperature of the reaction mixture. After 95 hours, the reaction was terminated in both systems. The conversion in the pervap-assisted esterification was found to be 93 percent, compared with the 75 percent conversion for the simple flask esterification.

Membrane selectivity for water over butanol was greater than 6000 and the average water flux was 0.36 kg/m$^2$/h, ranging from 1.04 kg/m$^2$/h at 6 percent water to 0.12 kg/m$^2$/h at 1.1 percent water. The invention also provides a method for esterifying a salt of a fermentation derived carboxylic acid comprising splitting the salt into its cationic and anionic part; mixing the anionic part with an alcohol to create a mixture; heating the mixture in the presence of a catalyst to create an ester; dehydrating the now heated mixture; and separating the ester from the now-dehydrated mixture. The step of splitting the salt into its cationic and anionic parts consists of subjecting the salt to mineral acid. The mineral acid is present in equimolar quantities to the anionic part. The organic acid is selected from the group consisting of lactic acid, butyric acid, succinic acid, acetic acid, propionic acid and combinations thereof. The alcohol is selected from the group consisting of methanol, ethanol, propanol, isopropanol, butanol and combinations thereof. The alcohol is mixed with the anionic part in a molar ratio selected from between 1:1 to 6:1. The mixture is heated to a temperature selected from a range of between approximately 75° C. to 150° C. The step of dehydrating the mixture consists of contacting the mixture to a pervaporation membrane selective to water so as to remove water from the mixture. The step of removing the ester from the now-dehydrated mixture consists of distilling the ester from the mixture. Alternatively, the step of removing ester from the now-dehydrated mixture consists of subjecting the now-dehydrated mixture to a pervaporation membrane selective to ester.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for esterifying ammonium carboxylate salt comprising:

a.) mixing the salt with an alcohol to create a mixture;

b.) heating the mixture in the presence of a catalyst; and c.) subjecting the mixture to a pervaporation process.

2. The method as recited in claim 1 wherein the ammonium carboxylate salt is an ammonium salt of an organic acid selected from the group consisting of lactic acid, propionic acid, butyric acid, acetic acid, succinic acid and combinations thereof.

3. The method as recited in claim 1 wherein the alcohol is mixed with the ammonium carboxylate salt in a mole ratio of between approximately 1:1 to 6:1.

4. The method as recited in claim 1 wherein the alcohol is selected from the group consisting of methanol, ethanol, propanol, isopropanol, butanol and combinations thereof.

5. The method as recited in claim 1 wherein the mixture is heated to a temperature selected from a range of between approximately 75° C. and 150° C.

6. The method as recited in claim 1 wherein the step of subjecting the mixture to a pervaporation process consists of contacting the mixture to a pervaporation membrane selective to ammonia and water so as to remove water and ammonia from the mixture to create a retentate fraction.

7. The method as recited in claim 6 wherein the retentate fraction is subjected to a pervaporation membrane selective to ester so as to remove ester from the retentate fraction.

8. The method as recited in claim 6 wherein the retentate fraction is subjected to distillation so as to remove ester from the retentate fraction.

9. A method for esterifying a salt of a fermentation derived carboxylic acid comprising:

a.) splitting the salt into its cationic and anionic part;

b.) mixing the anionic part with an alcohol to create a mixture;

c.) heating the mixture in the presence of a catalyst to create an ester;

d.) dehydrating the now heated mixture by contacting the mixture to a pervaporation membrane selective to water so as to remove water from the mixture; and e.) separating the ester from the now-dehydrated mixture.

10. The method as recited in claim 9 wherein the step of splitting the salt into its cationic and anionic parts consists of subjecting the salt to mineral acid.

11. The method as recited in claim 10 wherein the mineral acid is present in equimolar quantities to the anionic part.

12. The method as recited in claim 9 wherein the organic acid is selected from the group consisting of lactic acid, butyric acid, succinic acid, acetic acid, propionic acid and combinations thereof.

13. The method as recited in claim 9 wherein the alcohol is selected from the group consisting of methanol, ethanol, propanol, isopropanol, butanol and combinations thereof.

14. The method as recited in claim 9 wherein the alcohol is mixed with the anionic part in a molar ratio selected from between 1:1 to 6:1.

15. The method as recited in claim 9 wherein the mixture is heated to a temperature selected from a range of between approximately 75° C. to 150° C.

16. The method as recited in claim 9 wherein the step of removing the ester from the now-dehydrated mixture consists of distilling the ester from the mixture.

17. The method as recited in claim 9 wherein the step of removing ester from the now-dehydrated mixture consists of subjecting the now-dehydrated mixture to a pervaporation membrane selective to ester.

18. A method for esterifying amine carboxylate salt comprising:

a.) mixing the salt with an alcohol to create a mixture;

b.) heating the mixture in the presence of a catalyst; and c.) subjecting the mixture to a pervaporation process.

19. The method as recited in claim 18 wherein the alcohol is mixed with the amine carboxylate salt in a mole ratio of between approximately 1:1 to 6:1.

20. The method as recited in claim 18 wherein the alcohol contains from one to four carbons.

21. The method as recited in claim 18 wherein the mixture is heated to a temperature selected from a range of between approximately 75° C. and 150° C.

22. The method as recited in claim 18 wherein the step of subjecting the mixture to a pervaporation process consists of contacting the mixture to a pervaporation membrane selective to volatile amines so as to remove volatile amines and water from the mixture to create a retentate fraction.

23. The method as recited in claim 22 wherein the retentate fraction is subjected to a pervaporation membrane selective to ester so as to remove ester from the retentate fraction.

24. The method as recited in claim 22 wherein the retentate fraction is subjected to distillation so as to remove ester from the retentate fraction.

* * * * *